(12) United States Patent
Oikawa et al.

(10) Patent No.: US 8,953,870 B2
(45) Date of Patent: Feb. 10, 2015

(54) SURFACE INSPECTION DEVICE AND SURFACE INSPECTION METHOD

(75) Inventors: Satoshi Oikawa, Tochigi (JP); Satoshi Nojo, Tochigi (JP)

(73) Assignee: Honda Motor Co., Ltd., Tokyo (JP)

( * ) Notice: Subject to any disclaimer, the term of this patent is extended or adjusted under 35 U.S.C. 154(b) by 298 days.

(21) Appl. No.: 13/509,837

(22) PCT Filed: Oct. 4, 2010

(86) PCT No.: PCT/JP2010/005935
§ 371 (c)(1),
(2), (4) Date: May 15, 2012

(87) PCT Pub. No.: WO2011/061887
PCT Pub. Date: May 26, 2011

(65) Prior Publication Data
US 2012/0230579 A1  Sep. 13, 2012

(30) Foreign Application Priority Data

Nov. 18, 2009  (JP) .................................. 2009-262524

(51) Int. Cl.
*G06K 9/00* (2006.01)
*G01N 21/954* (2006.01)

(52) U.S. Cl.
CPC .................... *G01N 21/954* (2013.01)
USPC .......... 382/152; 348/92; 348/128; 356/237.2; 356/241.1; 356/426

(58) Field of Classification Search
USPC ........... 347/1–101; 382/141–152; 348/86–95, 348/125–134; 356/237.1–237.6, 426–431
See application file for complete search history.

(56) References Cited

U.S. PATENT DOCUMENTS 5,146,509 A * 9/1992 Hara et al. .................... 382/149
6,473,169 B1 * 10/2002 Dawley et al. ............. 356/239.4
(Continued)

FOREIGN PATENT DOCUMENTS

JP  5-346320 A  12/1993
JP  8-128960 A  5/1996
(Continued)

OTHER PUBLICATIONS

CN Office Action issued on Nov. 11, 2013 in the corresponding Chinese patent application.

*Primary Examiner* — Aaron W Carter
(74) *Attorney, Agent, or Firm* — Carrier Blackman & Associates, P.C.; Joseph P. Carrier; Jeffrey T. Gedeon

(57) ABSTRACT

A surface inspection device includes an image generator for generating a digital image achieved by imaging an inner surface of a bore which is subjected to a boring work, a line extraction processor for extracting a line along a horizontal direction set to a line extraction direction from the digital image, for determining the state of the inner surface of the bore based on the line extracted by the line extraction processor. The line extraction processor extracts lines along the line detection direction from respective digital images before and after rotation which are achieved by rotating the digital image once or over plural times every predetermined angle while the line extraction direction is fixed, and the estimating unit determines the state of the inner surface of the bore based on the lines extracted from the respective digital images before and after the rotation.

7 Claims, 9 Drawing Sheets

(56) References Cited

U.S. PATENT DOCUMENTS

| | | | |
|---|---|---|---|
| 2004/0119969 A1* | 6/2004 | Schleicher et al. | 356/237.1 |
| 2008/0033664 A1* | 2/2008 | Yamanoto et al. | 702/36 |
| 2009/0218509 A1* | 9/2009 | Ito et al. | 250/442.11 |
| 2012/0062728 A1* | 3/2012 | Oikawa et al. | 348/128 |
| 2012/0230579 A1* | 9/2012 | Oikawa et al. | 382/152 |
| 2013/0034293 A1* | 2/2013 | Xu et al. | 382/141 |

FOREIGN PATENT DOCUMENTS

| | | |
|---|---|---|
| JP | 2004-132900 A | 4/2004 |
| JP | 2004-264054 A | 9/2004 |
| JP | 2006-349598 A | 12/2006 |
| JP | 2008-209134 A | 9/2008 |
| JP | 2009-300287 A | 12/2009 |
| JP | 2010-019730 A | 1/2010 |

\* cited by examiner

FIG.3
(A)
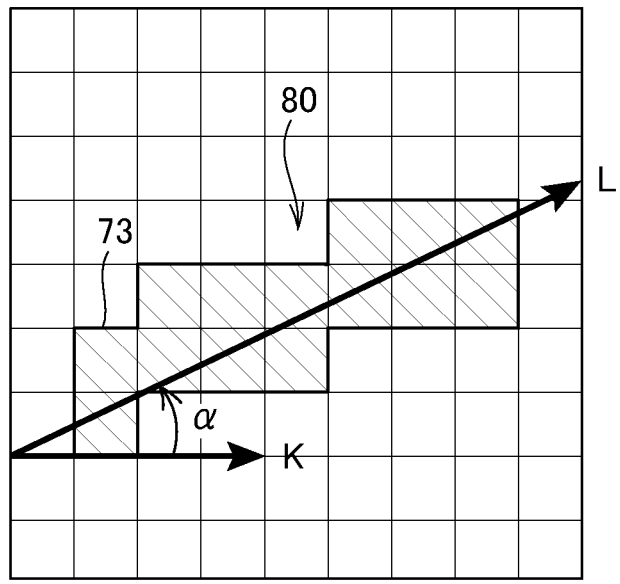
(B)
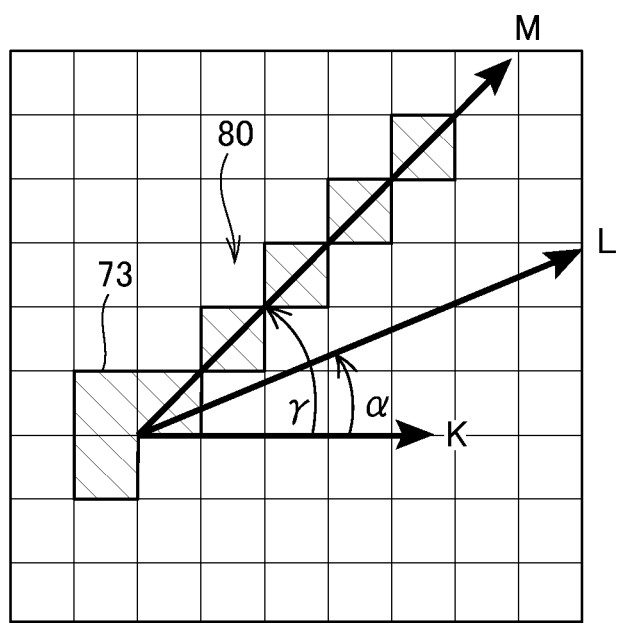

SURFACE INSPECTION DEVICE AND SURFACE INSPECTION METHOD

TECHNICAL FIELD

The present invention relates to a technique of inspecting the surface of a machined workpiece, and particularly to a technique of detecting linear flaws.

BACKGROUND ART

A boring work of forming a bore in a cylinder block of an engine is carried out in a process of manufacturing a vehicle. In the boring work, a tool for boring is made to advance to and retreat from a cylinder block to form a bore while the cutting tool is rotated, and thus a spiral machining mark (hereinafter referred to as "cross hatch") occurs on the inner surface of the bore. This cross hatch is used as a passage for engine oil (oil pit). When the surface roughness and surface property of the inner surface of the bore are deteriorated by the cross hatch, the sliding resistance of a piston sliding through the bore increases, so that it is impossible to make an engine have a desired performance. Therefore, after a boring is formed by the boring work, a honing work is generally executed to execute polish-finishing on the inner surface of the bore to the extent that an oil pit remains. After the honing work, a surface inspection to detect polishing residues on the inner surface of the bore is executed.

As a technique of inspecting the surface of a bore is known a method of imaging the inner surface of the bore to generate a digital image, binarizing the brightness values of the digital image on the basis of a predetermined threshold value and extracting lines regarded as polishing residues. Furthermore, in the extracting step of the lines, the mesh angle of the cross hatch is predetermined, and thus only lines extending along the angle concerned are set as extraction targets. Therefore, lines which are regarded as polishing residues of the machining mark are efficiently extracted (for example, see Patent Document 1).

PRIOR ART DOCUMENT

Patent Document

Patent Document 1: JP-A-2004-264054 (pages 8 and 9, FIG. 10).

SUMMARY OF THE INVENTION

Problem to be Solved by the Invention

However, it has been difficult for the prior art to detect flaws other than polishing residues such as dent, etc. Specifically, a flaw such as a dent or the like does not necessarily extend along the mesh angle of the cross hatch. Lines other than the mesh angle of the cross hatch are detected to detect such a flaw in the prior art, and thus it is necessary to thoroughly extract lines contained in a digital image. In this case, however, much time is required for image processing and the inspection time is long, which causes a problem that the productivity is lowered.

The present invention has been implemented in view of the foregoing situation, and has an object to provide a surface inspection device and a surface inspection direction that can also detect flaws extending in directions different from a fixed detection direction while flaws are detected in the fixed detection direction.

Means of Solving the Problem

In order to attain the above object, according to the present invention, there is provided a surface inspection device comprising : image generating means that generates a digital image achieved by imaging a surface of a machined workpiece; line extracting means that extracts a line corresponding to a flaw along a predetermined line detection direction from the digital image; and determining means that determines a surface state of the workpiece on the basis of the line extracted by the line extracting means, wherein the line extracting means rotates the digital image once or over plural times every predetermined angle while the line detection direction is fixed, and extracts lines along the line detection direction from respective digital images before and after the rotation, and the determining means determines the surface state of the workpiece on the basis of the lines extracted from the respective digital images before and after the rotation.

According to the present invention, the digital image is rotated once or over plural times every predetermined angle while the line detection direction is fixed, and the lines along the line detection direction are extracted from the respective digital images before and after the rotation. The surface state of the workpiece is determined on the basis of the lines extracted from the respective digital images before and after the rotation.

As described above, by extracting the lines along the predetermined line detection direction with respect to the digital images before and after the rotation, the flaws extending in the line detection direction are detected, and also the flaws extending in directions different from the line detection direction can be detected. The surface state is determined on the basis of the respective flaws, whereby the determination can be accurately performed.

Furthermore, according to the present invention, in the surface inspection device of the present invention, the extracting means rotates the digital image on the basis of an angle of a line intersecting to the line detection direction at the maximum angle among extractable lines having predetermined thicknesses when lines are extracted along the line detection direction.

According to the present invention, the rotation frequency of the digital image can be minimized, and the processing time can be further shortened.

According to the present invention, the surface inspection device of the present invention further comprises binarization processing means that performs binarization processing on the basis of brightness values of the digital image, and the line extracting means executes line extraction on the binarized digital image as a target.

According to the present invention, the digital images on which only the flaws to be extracted remain can be achieved by the binarization processing. Furthermore, the line extraction is executed on this digital image, and thus needless lines are not extracted, so that the processing time can be further shortened.

Furthermore, according to the present invention, the surface inspection device of the present invention further comprises coupling means that couples flaws separated from each other by a fixed amount in the line detection direction out of flaws displayed on the display image, and the line extracting means executes the line extraction on a digital image on which the flaws are coupled to each other by the coupling means.

According to the present invention, even when a flaw which is actually one extending flaw is displayed as severed lines or dots on the digital image due to the imaging state or the binarization processing, they are coupled to one another and extracted as one line. Therefore, the line which reflects the size of the flaw can be accurately extracted.

Furthermore, in order to attain the above object, according to the present invention, there is provided a surface inspection method comprising: a line extracting step that extracts a line corresponding to a flaw along a predetermined line detection direction from a digital image achieved by imaging a surface of a machined workpiece; and a determining step that determines a surface state of the workpiece on the basis of the line extracted in the line extracting step, wherein in the line extracting step, the digital image is rotated once or over plural times every predetermined angle while the line detection direction is fixed, and lines along the line detection direction are extracted from respective digital images before and after the rotation, and in the determining step, the surface state of the workpiece is determined on the basis of the lines extracted from the respective digital images before and after the rotation.

According to the present invention, there can be achieved the same action and effect as the surface inspection device according to the present invention.

Effect of the Invention

According to the present invention, the digital image is rotated once or over plural times every predetermined angle while the line detection direction is fixed, and the lines along the line detection direction are extracted from the respective digital images before and after the rotation. Therefore, the flaws extending in the directions different from the line detection direction can be also detected while the flaws extending in the line detection direction are detected. Furthermore, the surface state is determined on the basis of the respective flaws and thus the determination can be accurately performed.

In this case, the digital image is rotated on the basis of the angle of a line intersecting to the line detection direction at the maximum angle out of lines having predetermined thicknesses which are extractable when lines are extracted along the line detection direction, whereby the rotation frequency of the digital image can be minimized and thus the processing time can be further shortened.

Furthermore, in this case, the digital image is binarized on the basis of the brightness values, and the line extraction is executed on the binarized digital image, whereby extraction of needless lines is not executed and thus the processing time can be further shortened.

In this case, flaws which are separated from each other by a fixed amount in the line detection direction out of flaws displayed on the display image are coupled to each other, and the line extraction is executed on this digital image. Accordingly, even when an actually one extending flaw is displayed as severed lines or dots on the digital image due to an imaging state, binarization processing or the like, they are coupled and extracted as one line, and thus the line reflecting the size of the flaw can be accurately extracted.

BRIEF DESCRIPTION OF THE DRAWINGS

FIG. 2(A) shows an image before binarization processing, FIG. 2(B) shows an image after the binarization processing, and FIG. 2(C) shows an image after line extraction processing.

FIG. 3 is a diagram showing line extraction based on a continuing direction of dots corresponding to a flaw.

MODES FOR CARRYING OUT THE INVENTION

An embodiment according to the present invention will be described hereunder with reference to the drawings.

Figure 1:
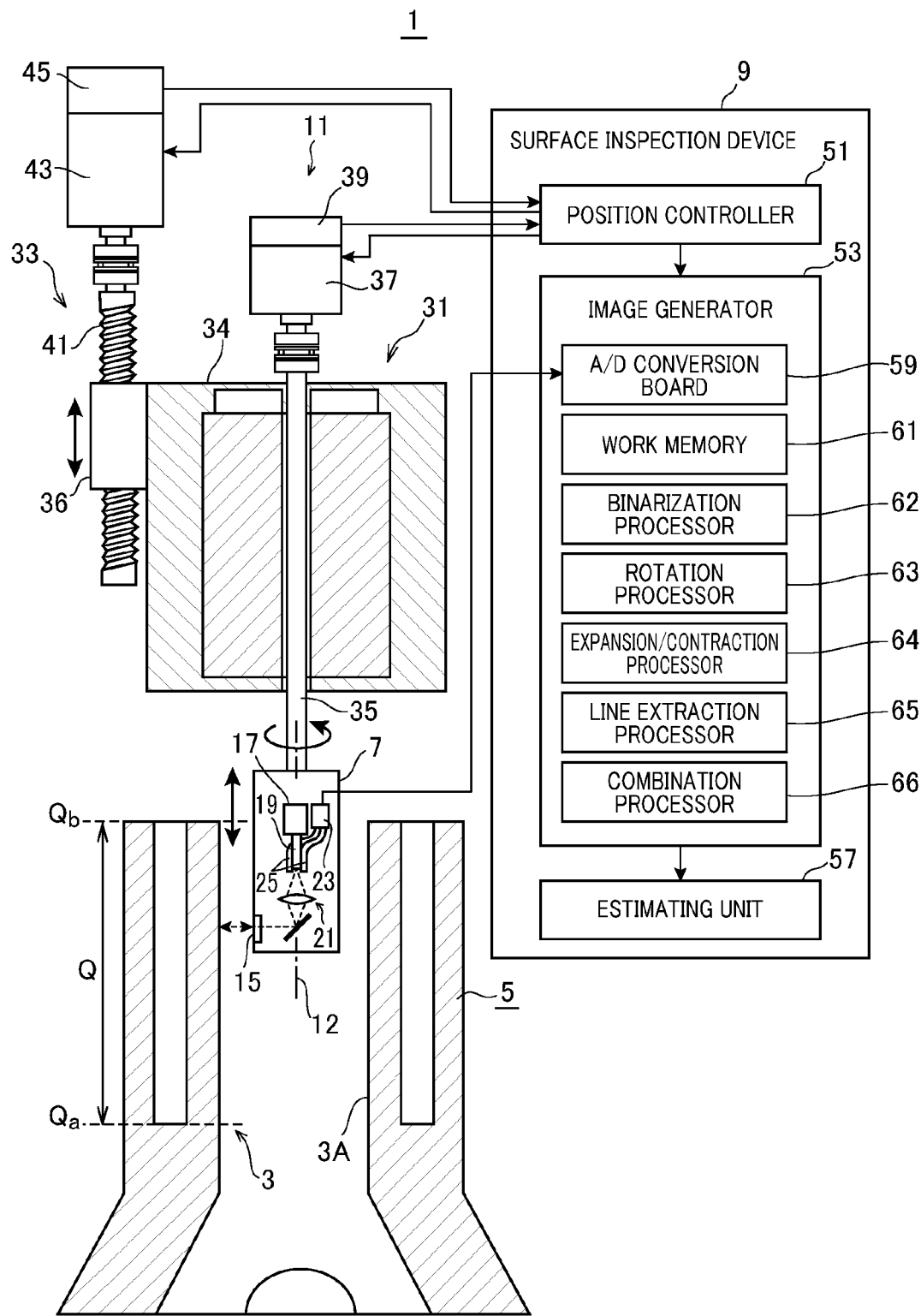
FIG. 1 is a diagram showing a bore inner surface inspecting system according to an embodiment of the present invention and the construction of a cylinder block having a bore as an inspection target formed therein.

FIG. 1 is a diagram showing a bore inner surface inspecting system 1 according to an embodiment of the present invention, and the construction of a cylinder block 5 having a bore 3 as an inspection target formed therein.

A bore 3 is formed by a so-called boring work in which a cutting tool is secured to a boring head provided to a rotational shaft so as to project in a radial direction from the boring head, and made to advance to and retreat from a cylinder block 5 as a workpiece while the boring head is rotated. Spiral cutting marks are formed on the inner surface 3A of the bore 3 through the boring work. Thereafter, a honing work is executed on the inner surface 3A of the bore 3 by using a processing head having a honing store mounted thereon so that surface roughness and surface property which enable an engine to have a desired performance are achieved while oil pits are left on the inner surface 3A of the bore 3.

The bore inner surface inspecting system 1 estimates the presence or absence of polishing residues on the basis of a digital image achieved by imaging the inner surface 3A of the bore 3 after the honing work. That is, the bore inner surface inspecting system 1 has a sensor head 7 for scanning the inner surface 3A of the bore 3, a surface inspection device 9 for generating a digital image on the basis of an output signal of the sensor head 7 and estimating the inner surface 3A of the bore 3 on the basis of the digital image, and a driving mechanism 11 for driving and moving the sensor head 7.

The sensor head 7 has such a hollow cylindrical shape that it can enter the bore 3, and it is secured to the driving mechanism 11 so as to be rotatable around a center axial line 12 and movable in a height direction and configured so as to sense the whole inner peripheral surface of the bore 3 while the height position thereof is changed. In the detailed construction of the sensor head 7, the sensor head 7 applies a laser beam from an opening 15 provided in the peripheral surface thereof to the inner surface 3A of the bore 3, detects a reflection light amount corresponding to the shape of a cutting mark and outputs the detected reflection light amount to the surface inspection device 9. That is, the sensor head 7 has LD (laser diode) 17 as a light source, an optical fiber 19 and a light condensing optical unit 21, and it guides light of LED 17 to the light condensing optical unit 21 through the optical fiber 19, condenses the light by the light condensing optical unit 21 and applies a laser beam from the opening 15 to the inner surface 3A of the bore 3. Furthermore, the sensor head 7 has a photodetecting sensor 23 for photodetecting reflection light, and also has plural optical fibers 25 that are disposed adjacently to the optical fiber 19 to guide reflection light returned from the inner surface 3A of the bore 3 through the light condensing optical unit 21 to the photodetecting sensor 23.

The driving mechanism 11 has a rotary drive mechanism 31 for rotating the sensor head 7, and an advance and retreat mechanism 33 for advancing and retreating the rotary drive mechanism 31.

The rotary drive mechanism 31 has a housing 34, a shaft 35 which has the sensor head 7 secured to the tip thereof and is provided so as to vertically penetrate through the housing 34, a shaft motor 37 for rotationally driving the shaft 35 under the control of the surface inspection device 9, and a rotary encoder 39 for detecting the rotational speed and rotational angle of the shaft 35 and outputting them to the surface inspection device 9.

The advance and retreat mechanism 33 is a feed screw mechanism, and has a threaded shaft portion 41, an advance and retreat motor 43 for rotationally driving the shaft portion 41 and a rotary encoder 45 for detecting the rotational speed and rotational angle of the shaft portion 41 and outputting them to the surface inspection device 9. The shaft portion 41 is threadably fitted in a nut portion 36 of the housing 34, and the shaft portion 41 is rotated by driving the advance and retreat motor 43 to advance and retreat the rotary drive mechanism 31.

the surface inspection device 9 has a position controller 51 for controlling the position of the sensor head 7 by controlling the driving mechanism 11, an image generator 53 for generating a digital image 70 of the inner surface 3A of the bore 3 on the basis of a photodetection signal of the sensor head 7 and extracting a line 81 (FIG. 2) corresponding to a flaw 80 (FIG. 2) such as a polishing residue, a dent or the like from the digital image 70, and an estimating unit (determining unit) 57 for determining the state of the inner surface 3A of the bore 3 from the flaw such as the polishing residue, the dent or the like based on an extraction result of the line 81 to estimate whether the flaw is good or bad. The surface inspection device 9 described above may be configured by making a personal computer execute a program for implementing the functions of respective units.

The position controller 51 contains a servo mechanism for driving the shaft motor 37 and the advance and retreat motor 43, and controls the position on the central axial line of the sensor head 7 and the rotational angle of the sensor head 7. That is, at an inspection start time, the position controller 51 inserts the sensor head 7 into the bore 3, and positions the opening 15 to the lower end position Qa of an inspection range Q. An operation of upwardly moving the sensor head 7 while rotating the sensor head 7 around the center axial line 12 so as to copy the locus of the boring tool in the boring work is executed until the opening 15 of the sensor head 7 reaches the upper end position Qb of the inspection range Q, thereby scanning the whole surface of the inspection range Q with the sensor head 7. The inspection range Q is determined by a range functioning as a sliding face of the cylinder.

The image generator 53 has an A/D conversion board 59 for executing A/D conversion on the photodetection signal from the sensor head 7 and outputting a digital signal representing brightness, and a work memory 61 which comprises, for example, a non-volatile memory such as RAM or the like and develops a digital image 70 based on the digital signal. Furthermore, the image generator 53 has a binarization processor 62, a rotation processor 63, an expansion/contraction processor (coupling means) 64, a line extraction processor 65 and a combination processor 66 as means for executing image processing on the digital image 70 of the work memory 61.

That is, the binarization processor 62 binarizes the digital image 70 of the work memory 61 by using a predetermined brightness value as a threshold value and extracts a flaw 80. The rotation processor 63 rotates the binarized digital image 70 by a predetermined angle. The line extraction processor 65 extracts lines corresponding to the flaw 80 from the respective digital images 70 before and after the rotation. The expansion/contraction processor 64 couples the lines 81 which are separated from each other by only a fixed amount in the detection direction of the lines 81, and the details of this processing will be described later. The combination processor 66 superimposes each of the lines 81 extracted from the pre-rotated and post-rotated digital images 70 on the digital image 70.

Figure 2:
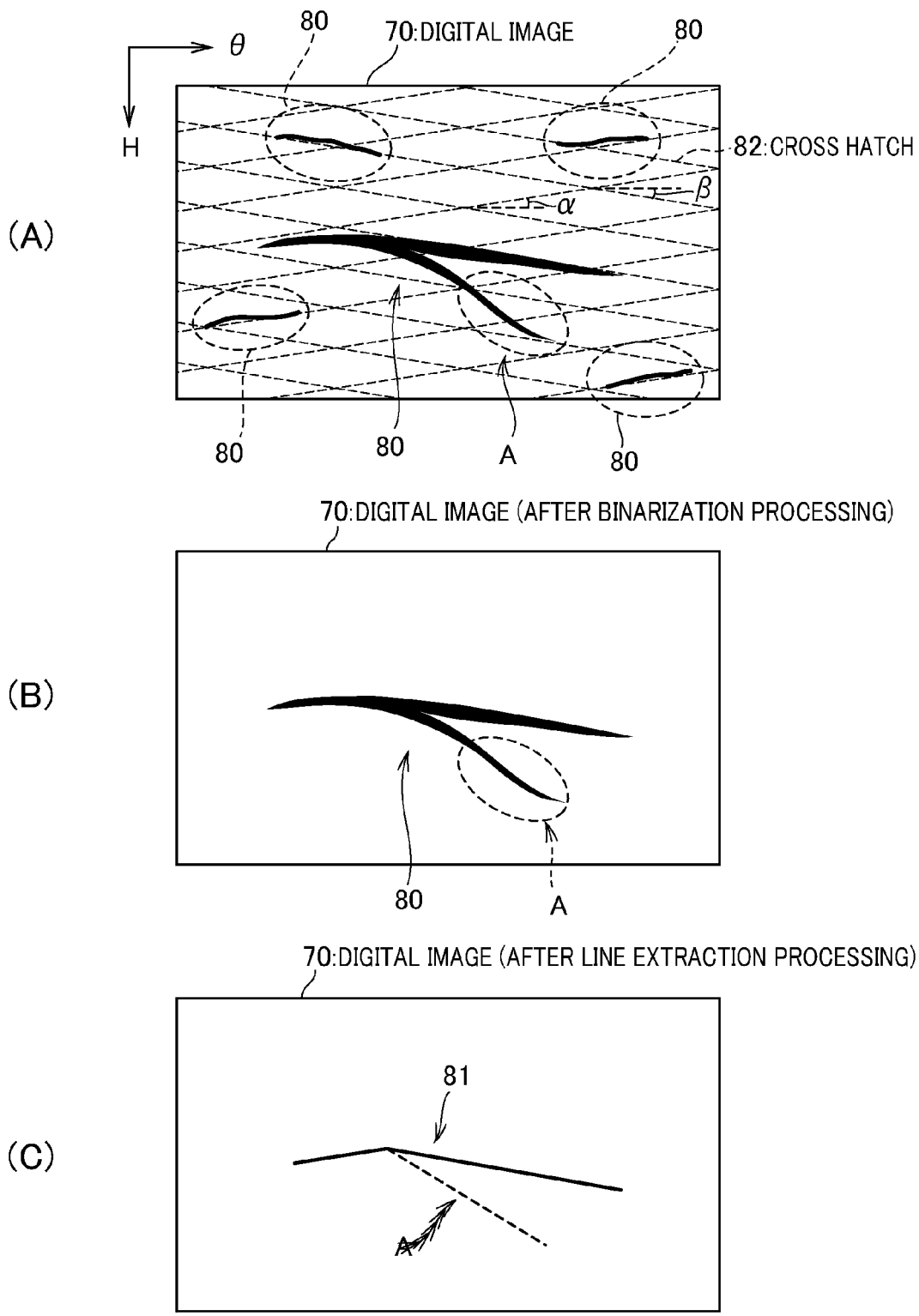
FIG. 2 is a diagram showing an example of a digital image.

FIG. 2 is a diagram showing an example of the digital image 70, wherein FIG. 2(A) shows an image before the binarization processing, FIG. 2(B) shows an image after the binarization processing, and FIG. 2(C) shows an image after the line extraction processing. The digital image 70 shown in FIG. 2(C) is apartially enlarged image of the inner surface 3A of the bore 3.

As described above, the digital image 70 is an image which is obtained by achieving reflection light intensities with the sensor head 7 at respective inspection positions in the bore 3, converting the thus-achieved reflection light intensities to brightness values in the A/D conversion board 59 and arranging these brightness values in correspondence to the inspection positions. The inspection positions are defined by the two-dimensional coordinate of the rotational angle $\theta$ and height position H of the sensor head 7. Therefore, as shown in FIG. 2(A), with respect to the vertical and horizontal axes of the digital image 70, the horizontal direction corresponds to the rotational angle $\theta$, and the vertical direction corresponds to the height H. When a flaw exists on the inner surface 3A of the bore 3, the reflection light intensity at the place of the flaw concerned decreases, and thus a place at which the brightness value is low in the digital image 70 can be regarded as a flaw 80.

In FIG. 2(A), dashed lines represents cross hatch 82. Not only the cross hatch 82 described above, but also an endless number of flaws 80 which are so small or shallow that no problem occurs in engine performance are detected in the digital image 70. A predetermined brightness value is set as a threshold value to discriminate the flaws 80 causing no problem from the flaws 80 to be detected as defects, and the binarization processor 62 executes binarization processing on the digital image 70 with the threshold value, thereby achieving the digital image 70 shown in FIG. 2(B).

In this digital image 70, the line extraction processor 65 extracts a line 81 extending along the flaw 80 from the digital image 70 as a criterion for determining whether any flaw 80 exists or not. That is, as shown in FIG. 2(C), when the line 81 is extracted, it is indicated that a flaw 80 to be detected as a defect is displayed on the digital image 70, and in the other case, it is indicated that such a flaw 80 is not displayed. The estimating unit 57 detects extraction or non-extraction of any line 81 and further detects the presence or absence of a flaw 80 to be detected as a defect such as a polishing residue or a dent on the inner surface 3A of the bore 3 on the basis of the length of the line 81 or the like, and estimates on the detection result whether the inner surface 3A is good or not.

In the line extraction processing of the line extraction processor 65, the line 81 is extracted as follows in order to short the processing time of the line extraction and simplify an algorithm. That is, cutting dents caused by the boring work for the bore 3 are formed as regularly arranged lines like the cross hatch 82. That is, the flaw 80 corresponding to a polishing residue occurs on a line of the cross hatch 80, and thus the flaw 80 concerned extends along the direction of the cross hatch 82. Accordingly, in the line extraction processing, the flaw 80 corresponding to the polishing reside can be detected by extracting the line 81 along the direction of the cross hatch 82 from the digital image 70. The extraction of the line 81 as described above is performed as follows. For example, when the mesh angle of the cross hatch 82 (hereinafter referred to as "cross hatch angles") based on a horizontal direction K is represented by α and β, the extraction of the line 81 is performed by determining whether a binarized digital image 70 has a place at which pixels (hereinafter referred to as "dots") 73 having brightness values representing a flaw 80 continuously exist in the directions of the cross hatch angles α and β. For example, when dots 73 are continuous with one another along a line L whose gradient corresponds the cross hatch angle α, β as shown in FIG. 3(A), an assembly of these dots 73 is extracted as a line 81.

However, in a case where the line extraction is performed on the basis of the cross hatch angles α and β, when an extension direction M of the linearly arranged dots 73 is out of the line L whose gradient corresponds to the cross hatch angle α, β as shown in FIG. 3(B), the line 81 comprising a group of these dots 73 is not extracted. Therefore, as shown in FIG. 2(A) to FIG. 2(C), a flaw 80 (represented by an arrow A in the figures) such as a dent or the like which extends to be deviated from the directions of the cross hatch angles α and β out of flaws 80 to be detected as defects may be omitted as a result of the line extraction processing, and thus the bore 3 cannot be accurately estimated.

Therefore, according to this embodiment, the digital image 70 is rotated, and the line extraction processing is executed on the respective digital images 70 before and after the rotation on the basis of the cross hatch angles α and β. Accordingly, a line 81 which is deviated from the cross hatch angles α and β can be extracted, and thus extraction leakage of the line 81 corresponding to the flaw 80 can be prevented. As the step angle of the rotational angle of the digital image 70 which is to be subjected to the line extraction processing is smaller, it is expected that the extraction precision of the line 81 can be enhanced, however, it causes the processing time to be remarkably long.

Therefore, according to this embodiment, the processing time is shortened as follows.

Figure 4:
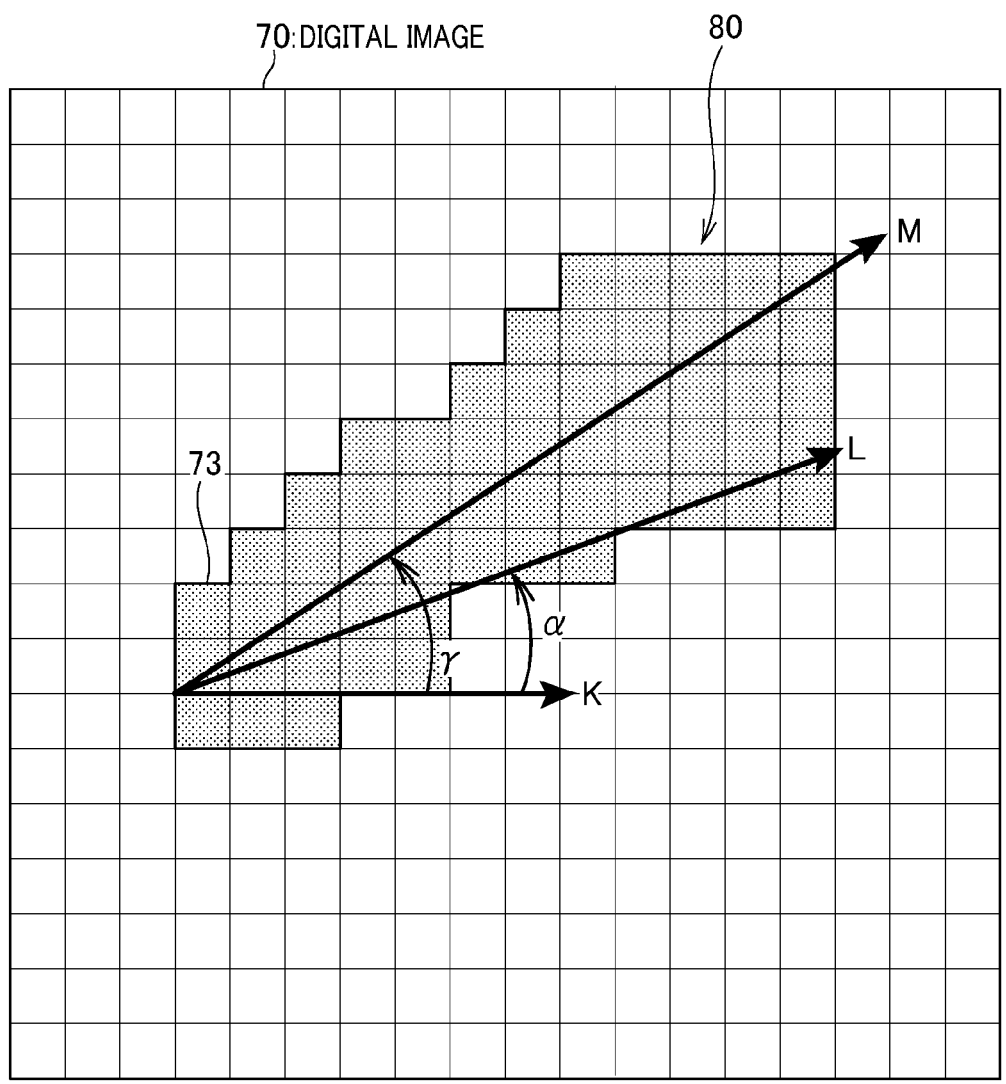
FIG. 4 is a diagram showing line extraction of a flaw having a large opening width.

Even when the extension direction M of the flaw 80 is deviated from the cross hatch angles α and β, there is a case where the line 81 is extracted in accordance with the thickness of the flaw 80. Here, the thickness of the flaw 80 means an open width in the traverse direction of the flaw 80 extending linearly. That is, in a case where the open width of the flaw 80 is large, the straight line L extending at the cross hatch angle α is contained within the area of the flaw 80 even when the extension direction M of the flaw 80 is distant from the straight line L as shown in FIG. 4. In this case, the line 81 corresponding to the flaw 80 concerned is detected even when the extension direction M of the flaw 80 is deviated from the cross hatch angle α, β.

As described above, in the line extraction processing in which the flaw 80 extending in the direction of the cross hatch angle α, β is extracted as the line 81 by detecting the dots 73 which are continuous with each other in the direction of the cross hatch angle α, β, when the extension direction M of the flaw 80 is deviated from the cross hatch angle α, β, it is determined on the basis of the size of the open width of the flaw 80 whether it can be detected as the line 81.

In other words, by rotating the digital image 70 with reference to the extension direction M of the flaw 80 which can be extracted as the line 81, the line 81 corresponding to the flaw 80 can be surely extracted with a small frequency of rotations without rotating the digital image 70 little by little, and thus the processing time can be shortened.

Figure 5:
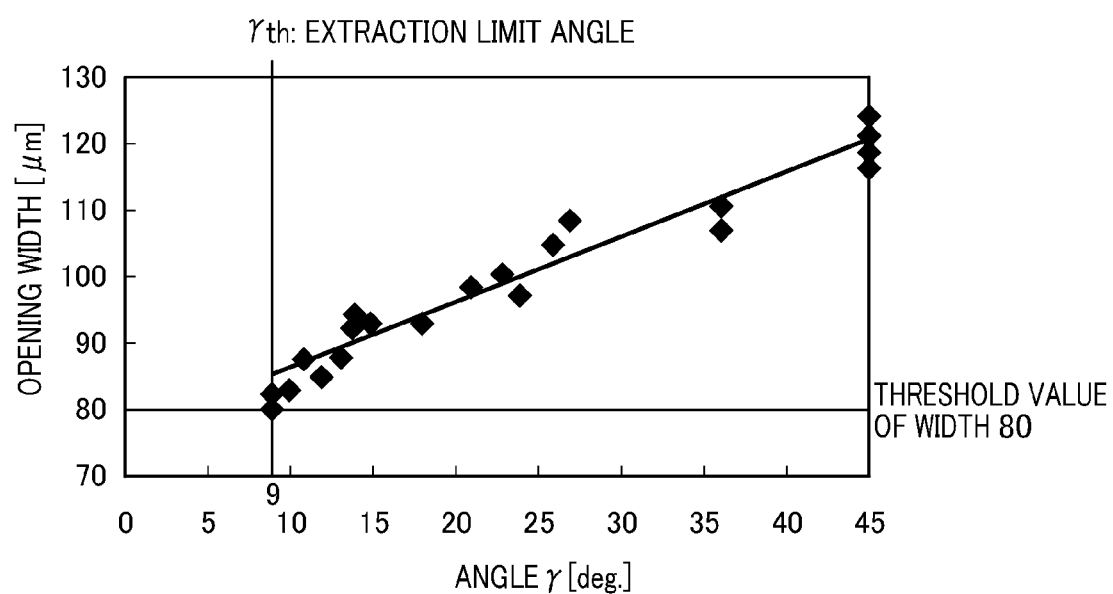
FIG. 5 is a diagram showing an example of the relationship between the opening width of a flaw extractable as a line and an extension direction thereof when a flaw in the horizontal direction is detected.

FIG. 5 is a diagram showing an example of the relationship between the open width of a flaw 80 extractable as a line 81 and the extension direction M thereof when the flaw 80 extending in the horizontal direction K is detected. In FIG. 5, the extension direction M of the flaw 80 is represented by an angle γ based on the horizontal direction K.

As shown in FIG. 5, it is found that as the open width of the flaw 80 is larger, the line 81 corresponding to the flaw 80 can be detected even when the extension direction M of the flaw 80 is deviated from the horizontal direction K.

Therefore, the minimum open width of flaws 80 to be extracted as defects is determined, and a limit angle at which the flaw 80 corresponding to the open width concerned can be extracted (hereinafter referred to as "extraction limit angle") γth is determined experimentally or the like in advance. Furthermore, when the digital image 70 is rotated to extract lines from the digital image 70, the digital image 70 is rotated in consideration of the extraction limit angle γth, whereby the line 81 corresponding to the flaw 80 can be surely extracted. In this embodiment, the minimum open width of the flaws 80 to be detected as the defects is set to 80 μm, and the extraction limit angle γth is set to 9 [deg] on the basis of an experimental result of FIG. 5.

The cross hatch angles α and β are defined by processing conditions such as the bore diameter, the stroke, the frequency, the number of revolutions, etc. in the boring work using the boring tool, and under the same processing conditions, substantially the same cross hatch angles α and β are provided.

In this embodiment, under a condition that the bore diameter is equal approximately to about 80 mm, the stroke is equal to about 80 mm, the frequency is equal to 2.5 Hz to 3 Hz and the number of revolutions is equal to 420 rpm to 600 rpm, the cross hatch angles α and β are determined as 18° and −18°. That is, in this embodiment, the extension direction M of the flaw 80 corresponding to the polishing residue is estimated to be about ±18°.

In the line extraction processing of this embodiment, the horizontal direction K is set to the line detection direction, and flaws 80 extending in the line detection direction are extracted. The extension direction M of the flaw 80 corresponding to the polishing residue is out of the range of the extraction limit angle γth=9 [deg]. Therefore, in the line extraction processing, in order to surely detect the polishing residue from the digital image 70, an image rotation angle δ of the digital image 70 is determined so that the extension direction M of the flaw 80 corresponding to the polishing residue is not more than the extraction limit angle γth. That is, in this embodiment, the image rotation angle δ is set to values of 0°, ±15°.

In the line extraction processing, continuity in the horizontal direction K of dots 73 representing a flaw 80 is extracted as a line 81 in the digital image 70 as described above. Therefore, when some gap occurs between the dots 73, they are not extracted as a line 81. Furthermore, when a gap occurs between lines 81, the lines 81 are divisionally detected, and thus the size of the flaw 80 may be inaccurately detected. Therefore, when the gap (interval amount) between dots 73 or between lines 81 in the horizontal direction K is small, these are coupled into one line 81, and thus the expansion/contraction processor for performing the expansion/contraction processing is provided.

Figure 6:
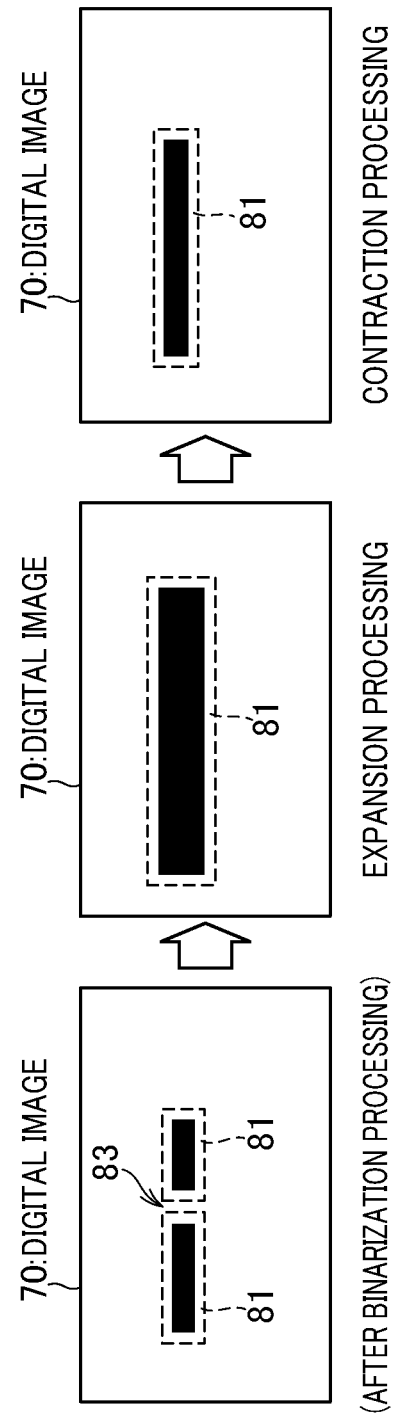
FIG. 6 is a diagram showing an example of expansion/contraction processing.

FIG. 6 is a diagram showing an example of the expansion/contraction processing.

According to the expansion/contraction processing, expansion processing is first executed to change pixels in a predetermined range to dots 73 corresponding to a flaw 80 with each dot of the line 81 corresponding to the flaw 80 set as the center of the range. As a result, as shown in FIG. 6, lines 81 which are severed from each other through a fixed amount of gap 83 in the horizontal direction K are coupled to each other, and one thick line 81 (the range of the line is expanded) is achieved. Subsequently, contraction processing is secondly executed to contract the expanded line 81 till an original thickness with keeping the coupled portion. Accordingly, the gap 83 is coupled, and the lines 81 which are severed from each other in the horizontal direction K are coupled into one line 81. In the expansion processing, how degree the line 81 should be made thick is predetermined in accordance with the size of the gap 83 to be filled.

Subsequently, the surface inspection operation for the bore 3 by the surface inspection device 9 will be described.

Figure 7:
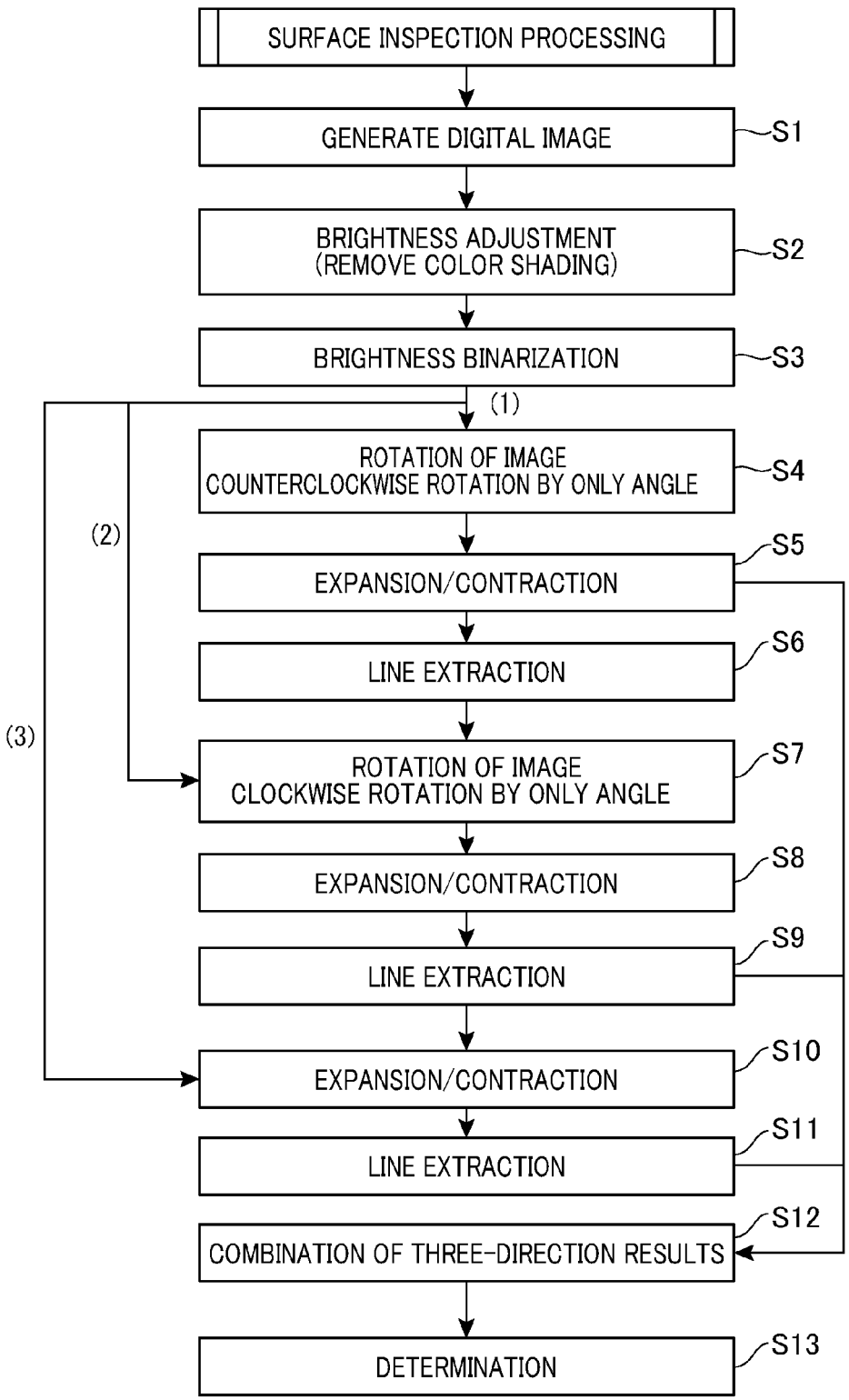
FIG. 7 is a flowchart showing surface inspection processing of a surface inspection device.

FIG. 7 is a flowchart of the surface inspection processing of the surface inspection device 9.

As shown in FIG. 7, in the surface inspection processing, the image generator 53 first generates the digital image 70 of the inner surface 3A of the bore 3 in the work memory 61 (step S1). Subsequently, various kinds of image processing on the digital image 70 are executed at high speed on the work memory 61. Subsequently, the brightness of the digital image 70 is adjusted so that the image generator 53 accurately extracts the flaw 80 through the binarization processing (step S2).

Figure 8:
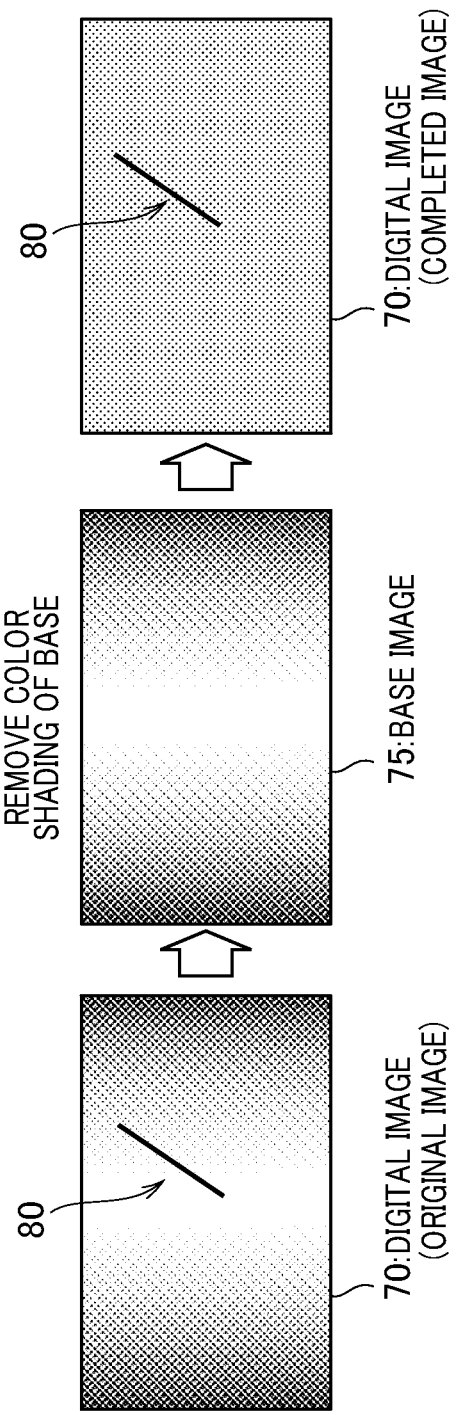
FIG. 8 is a diagram showing an example of adjustment of brightness.

FIG. 8 is a diagram showing an example of the brightness adjustment.

In the brightness adjustment, a base image 75 which is an image achieved by excluding a flaw 80 from the digital image 70 is generated on the basis of brightness values which are regarded as the dots 73 corresponding to the flaw 80. Subsequently, the brightness adjustment is performed so that color shading of the base image 75 disappear, and then the previously excluded flaw 80 is combined, thereby achieving the digital image 70 whose base is uniformly bright.

Returning to FIG. 7, the binarization processor 62 generates, on the work memory 61, a digital image 70 achieved by subjecting the brightness-adjusted digital image 70 to the binarization processing based on the brightness values to extract the flaw 80 (step S3). Thereafter, this digital image 70 is targeted to be subjected to the extraction processing of the line 81 corresponding to the flaw 80.

Figure 9:
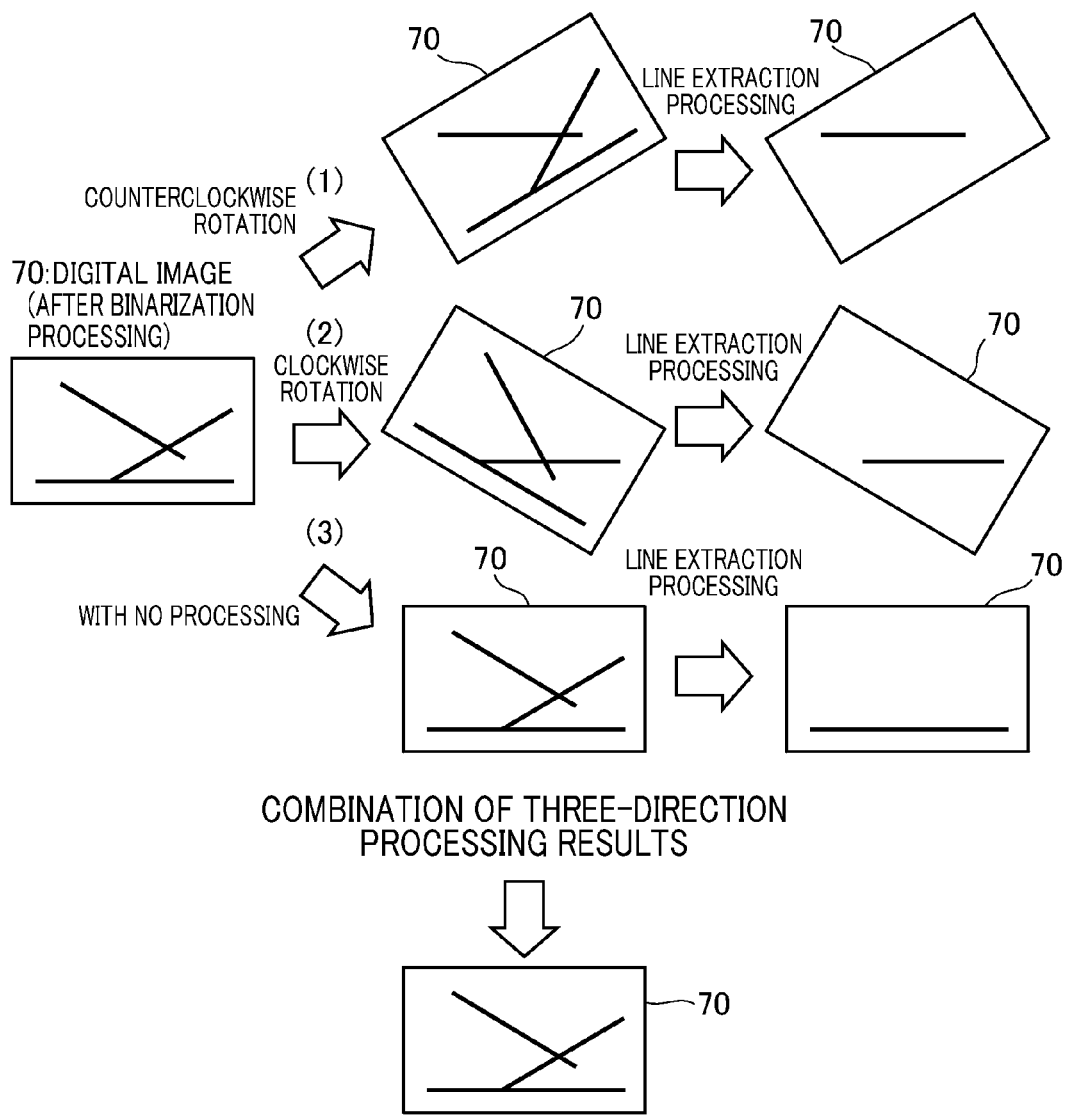
FIG. 9 is a diagram showing line extraction processing.

FIG. 9 is a diagram showing the extraction processing of the line 81.

As shown in FIG. 9, in the extraction processing of the line 81, the binarized digital image 70 is rotated counterclockwise and clockwise, and the line 81 is extracted with respect to each of digital images 70 after the respective rotations. In addition, the extraction of the line 81 is also executed on an original digital image 70 which is not rotated. The lines 81 which are achieved by the line extraction processing on the respective digital images 70 are combined with one another to achieve a digital image 70 on which the lines 81 are superimposed.

The processing procedure described above will be described with reference to FIG. 7. As shown in FIG. 7, the rotation processor 63 first rotates the digital image 70 counterclockwise by only an image rotational angle δ (step S4).

The expansion/contraction processor 64 executes the expansion/contraction processing on the digital image 70 which has been counterclockwise rotated (step S5), and the line extraction processor 65 executes the line extraction processing on the digital image 70 which has been subjected to the expansion/contraction processing (step S6). In this line extraction processing, a flaw 80 extending in the horizontal direction on the digital image 70 is set as a detection target.

That is, a place at which the dots 73 having brightness values representing a flaw 80 are continuous with one another in the horizontal direction is extracted as a line 81. At this time, a flaw 80 which extends to have a gradient with reference to the horizontal direction is also detected with high precision when the gradient 81 is not more than the extraction limit angle γth.

That is, in a case where the dots 73 are also continuous with one another in the vertical direction and an assembly area of the dots 73 has a width in the vertical direction, when the width in the vertical direction of the assembly area of the dots 73 is set within the range of the open width (80 μm in this embodiment) of a flaw 80 which is determined to be extracted as a defect, a flaw 80 extending within the range of the extraction limit angle γth (±9° in this embodiment) with reference to the horizontal direction is also detected.

As a result, as shown in FIG. 9, a line 81 corresponding to a flaw 80 which intersects to the horizontal direction at an angle of the extraction limit angle γth or less out of many flaws 80 is surely extracted from the counterclockwise rotated digital image 70.

Subsequently, in order to extract a line 81 from the clockwise rotated digital image 70, the rotation processor 63 clockwise rotates the digital image 70 by only the image rotational angle δ (step S7), and the expansion/contraction processor 64 executes the expansion/contraction processing on the clockwise rotated digital image 70 (step S8) as shown in FIG. 7. Then, the line extraction processor 65 executes the line extraction processing on the digital image 70 which has been subjected to the expansion/contraction processing (step S9).

In order to extract a line 81 from the digital image 70 before the rotation, the expansion/contraction processor 64 executes the expansion/contraction processing on the digital image 70 before the rotation (step S10), and the line extraction processor 65 executes the line extraction processing on the digital image 70 which has been subjected to the expansion/contraction processing (step S11).

The combination processor 66 superimposes the lines 81 extracted from the respective three digital images 70 of the counterclockwise rotated digital image, the clockwise rotated digital image and the non-rotated digital image to compose a digital image 70 (step S12). At this time, with respect to the lines 81 extracted from the digital images after the rotation, the lines 81 are reversely rotated and superimposed to make the digital image 70 before the rotation set as a reference. On the basis of the state of the inner surface 3A of the bore 3 based on the presence or absence of the lines 81 in the digital image 70 and the length, number, etc. of the lines 81, the estimating unit 57 determines whether the bore is defective or not. Flaws 80 extending in various extension directions are displayed on the original digital image 70 and these flaws 80 are drawn as lines 81 on the digital image 70 which the estimating unit 57 uses for the determination. Therefore, the estimation can be performed by using such a digital image 70, and thus the defectiveness or non-defectiveness of the bore 3 can be accurately determined.

As described above, according to this embodiment, the line extraction processor 65 rotates the digital image 70 counterclockwise and clockwise every image rotational angle δ while the line detection direction is fixed to the horizontal direction K, and extract lines 81 along the horizontal direction K from each of the digital images 70 before and after the rotation. The estimating unit 57 determines the state of the inner surface 3A of the bore 3 on the basis of the lines 81 extracted from each of the digital image 70 before and after the rotation.

According to this construction, the lines 81 are extracted along the horizontal direction K from each of the digital images 70 before and after the rotation, whereby flaws 80 extending in directions different from the horizontal direction K can be detected while flaws 80 extending in the horizontal direction K are detected. Accordingly, the surface state is determined on the basis of the respective flaws 80, whereby the defectiveness or non-defectiveness of the bore 3 can be accurately determined.

Furthermore, according to this embodiment, in a case where lines 81 are extracted along the horizontal direction K, out of extractable lines 81 whose open widths are to be detected as flaws 80, the angle of a line 81 which intersects to the horizontal direction K at the maximum angle is set as the extraction limit angle γth, and the digital image 70 is rotated on the basis of the extraction limit angle γth.

According to this construction, the rotation frequency of the digital image 70 can be minimized, and the processing time required for the line extraction can be further shortened.

Furthermore, according to this embodiment, the digital image 70 is subjected to the binarization processing based on the brightness values thereof, and then the extraction of lines 81 is executed on the binarized digital image 70.

According to this construction, a digital image 70 on which only flaws 80 to be extracted remain is achieved by the binarization processing. This digital image 70 is targeted to be subjected to the line extraction, whereby the processing time required for the line extraction can be further shortened because extraction of needless lines is not executed.

Still furthermore, according to this embodiment, out of the flaws 80 displayed on the digital image 70, flaws 80 which are separated from each other by a fixed amount in the horizontal direction K are coupled with each other, and then the extraction of the line 81 is executed.

According to this construction, even when a flaw 80 which is actually one extending flaw 80 is displayed as severed lines 81 or dots (dots 73) on the digital image 70 due to the imaging state or the binarization processing, they are coupled to one another and extracted as one line 81. Therefore, the line 81 which reflects the size of the flaw 80 can be accurately extracted.

The above embodiment merely represents an example of the present invention, and any modification and application may be made without departing from the subject mater of the present invention.

For example, in the above embodiment, the digital image 70 is rotated after the binarization processing is executed. However, the present invention is not limited to this style, and the binarization processing may be executed every time the digital image 70 is rotated, or before the line extraction processing when the digital image 70 is not rotated. Accordingly, even when the pixel values of the digital image 70 may vary due to the rotation of the digital image 70, the lines 81 can be extracted without being affected by the variation concerned.

Furthermore, in the above embodiment, the frequency of rotations based on the image rotational angle δ of the digital image 70 is set to once in each of the counterclockwise rotation and the clockwise rotation. However, the digital image 70 may be rotated in each of the counterclockwise and clockwise directions or in one of the directions at n times while the image rotational angle δ is multiplied by n (n=2, 3, ..., ).

Still furthermore, in the above embodiment, the line extraction direction is set to the horizontal direction K. However, the embodiment is not limited to this style, and the line extraction direction may be fitted to the cross hatch angle α, β.

Furthermore, in the above embodiment, a bore formed by cutting a cylinder of an engine is exemplified as an inspection target of the surface inspection device 9 according to this invention. However, the present invention is not limited to this style, and the present invention may be broadly applied to inspection of the surface state of a work which is cut in one direction, particularly inspection of flaw detection.

DESCRIPTION OF REFERENCE NUMERALS

1 bore inner surface inspection system
3 bore
3A inner surface
7 sensor head
9 surface inspection device
23 photodetecting sensor
31 rotary drive mechanism
33 advance/retreat mechanism
51 position controller
53 image generator
57 estimating unit (determining means)
61 work memory
62 binarization processor (binarization processing means)
63 rotation processor
64 expansion/contraction processor (coupling means)
65 line extraction processor (line extracting means)
66 combination processor
70 digital image
80 flaw
81 line
82 cross hatch
K horizontal direction (line extraction direction)
M extension direction
γth extraction limit angle

The invention claimed is:

1. A surface inspection device comprising:
  image generating means that generates a digital image achieved by imaging a surface of a machined workpiece;
  line extracting means that extracts a line corresponding to a flaw along a predetermined line detection direction from the digital image; and
  determining means that determines a surface state of the workpiece on the basis of the line extracted by the line extracting means, wherein the line extracting means rotates the digital image once or over plural times every predetermined angle while the line detection direction is fixed, and extracts lines along the line detection direction from respective digital images before and after the rotation, the determining means determines the surface state of the workpiece on the basis of the lines extracted from the respective digital images before and after the rotation, and the respective digital images before and after the rotation shows a same area on the surface of the machined workpiece.

2. The surface inspection device according to claim 1, wherein the extracting means rotates the digital image on the basis of an angle of a line intersecting to the line detection direction at the maximum angle among extractable lines having predetermined thicknesses when lines are extracted along the line detection direction.

3. The surface inspection device according to claim 1, further comprising binarization processing means that performs binarization processing on the basis of brightness values of the digital image, wherein the line extracting means executes line extraction on the binarized digital image as a target.

4. The surface inspection device according to claim 1, further comprising coupling means that couples flaws separated from each other by a fixed amount in the line detection direction out of flaws displayed on the display image, wherein the line extracting means executes the line extraction on a digital image as a target on which the flaws are coupled to each other by the coupling means.

5. A surface inspection method comprising:
   a line extracting step that extracts a line corresponding to a flaw along a predetermined line detection direction from a digital image achieved by imaging a surface of a machined workpiece; and
   a determining step that determines a surface state of the workpiece on the basis of the line extracted in the line extracting step, wherein in the line extracting step, the digital image is rotated once or over plural times every predetermined angle while the line detection direction is fixed, and lines along the line detection direction are extracted from respective digital images before and after the rotation, in the determining step, the surface state of the workpiece is determined on the basis of the lines extracted from the respective digital images before and after the rotation, and the respective digital images before and after the rotation shows a same area on the surface of the machined workpiece.

6. The surface inspection device according to claim 1, comprising a combination processor superimposing each of the lines extracted from the respective digital images before and after the rotation on the digital image,
   wherein the combination processor reversely rotates the lines extracted from the digital images after the rotation to superimpose on the digital image.

7. The surface inspection device according to claim 1, wherein the respective digital images before and after the rotation shows a same part of the surface of the machined workpiece.

* * * * *